United States Patent
Goutsis et al.

(10) Patent No.: US 8,430,935 B2
(45) Date of Patent: Apr. 30, 2013

(54) COLORANTS FOR KERATINIC FIBRES HAVING OPTIMIZED VISCOSITY ADJUSTMENT

(75) Inventors: Konstantin Goutsis, Juechen (DE); Frank Janssen, Neuss (DE); Marc Krippahl, Moenchengladbach (DE)

(73) Assignee: Henkel AG & Co. KGAA (DE)

( * ) Notice: Subject to any disclaimer, the term of this patent is extended or adjusted under 35 U.S.C. 154(b) by 0 days.

(21) Appl. No.: 13/613,376

(22) Filed: Sep. 13, 2012

(65) Prior Publication Data

US 2013/0042882 A1 Feb. 21, 2013

Related U.S. Application Data

(63) Continuation of application No. PCT/EP2010/068807, filed on Dec. 3, 2010.

(30) Foreign Application Priority Data

Mar. 25, 2010 (DE) .......................... 10 2010 003 265

(51) Int. Cl.
*A61Q 5/10* (2006.01)
(52) U.S. Cl.
USPC ................ 8/405; 8/406; 8/431; 8/435; 8/552; 8/558
(58) Field of Classification Search .............. 8/405, 406, 8/431, 435, 552, 558
See application file for complete search history.

(56) References Cited

U.S. PATENT DOCUMENTS 4,927,627 A * 5/1990 Schrader et al. ................ 424/62
2012/0312318 A1 12/2012 Krippahl et al.

FOREIGN PATENT DOCUMENTS

| WO | 9118584 A1 | 12/1991 |
| WO | 013450 A2 | 2/2003 |
| WO | 116844 A2 | 9/2011 |

OTHER PUBLICATIONS

European Patent Office, International Searching Authority, "International Search Report" mailed Dec. 6, 2012; International Appln. No. PCT/US2010/068807, filed Dec. 3, 2010.
Schrader, Karlheinz, "Very Core Basics and Recipes of Cosmetics", 1989.

* cited by examiner

*Primary Examiner* — Eisa Elhilo
(74) *Attorney, Agent, or Firm* — Ingrassia Fisher & Lorenz PC

(57) ABSTRACT

A multi-component packaging unit includes a first container containing a color changing preparation comprising, in a cosmetic carrier, a color-changing component and a second container packaged separately from the first container and containing an oxidizing agent preparation. The oxidizing agent preparation comprises at least two phases separated from one another. A first phase has an aqueous phase that comprises, in a cosmetically acceptable carrier, a chemical oxidizing agent and an anionic polymeric thickener chosen from homo- and copolymers of acrylic acid and methacrylic acid. A second phase has a hydrophobic phase that comprises an oil chosen from paraffin oil, liquid carboxylic acid esters of $C_2$ to $C_8$ monoalkanol with a mono- or dicarboxylic acid, and combinations thereof.

15 Claims, No Drawings

COLORANTS FOR KERATINIC FIBRES HAVING OPTIMIZED VISCOSITY ADJUSTMENT

CROSS-REFERENCE TO RELATED APPLICATION

This application is a continuation of International Application No. PCT/EP2010/068807, filed Dec. 3, 2010, which was published under PCT Article 21(2) and which claims priority to German Application No. 10 2010 003 265.4, filed Mar. 25, 2010, which are all hereby incorporated in their entirety by reference.

TECHNICAL FIELD

The technical field is an oxidizing coloring preparation for keratinic fibers, in particular human hair, that possesses improved viscosity. This viscosity improvement is achieved by the interaction of an anionic polymeric thickener in combination with an oil phase, the anionic polymeric thickener and the oil being present in two mutually separated phases of a developer preparation containing at least a chemical oxidizing agent.

BACKGROUND

Modification of the shape and color of hair represents an important sector of modern cosmetology. The appearance of the hair can thereby be adapted both to current fashion trends and to the individual desires of the particular person. These agents are intended to bring about not only the desired color and shaping performance, but also the minimum possible damage to the hair, and by preference should in fact possess additional care-providing properties.

One skilled in the art knows of a variety of coloring systems, depending on the requirements for the coloring process, for making available color-changing cosmetic agents, in particular for the skin or keratin-containing fibers such as, for example, human hair. So-called oxidative coloring agents are used for permanent, intense colors having corresponding fastness properties. Such coloring agents usually contain oxidation dye precursors, so-called developer components and coupler components, which, under the influence of oxidizing agents or atmospheric oxygen, form among one another the actual dyes. It is therefore usual to use two-part coloring agents from which the utilization mixtures are produced only just before utilization, from a color changing preparation and an oxidizing agent preparation. These oxidizing coloring agents are notable for outstanding, long-lasting color results. For temporary coloring, it is usual to use coloring or toning agents that contain so-called substantive dyes ("direct absorbers") as a coloring component.

In order to produce optimum coloring performance, oxidizing coloring agents as a rule require an alkaline pH for thorough coloring, in particular between pH 9.0 and pH 10.5. In addition, the application period for attractive coloring results is usually between 10 and 45 minutes. It is therefore necessary for the ready-for-use coloring agent to be formulated and packaged in such a way that the coloring agent on the one hand can readily be distributed onto the keratinic fibers to be colored, but on the other hand remains during the application time in the fibers to be colored. It is advantageous for this if the coloring agent has a specific viscosity that enables application of the agent but allows the agent to remain at the location of use. This viscosity can be established in the ready-for-use coloring agent by means of polymeric thickeners; that thickener can be contained both in the color changing preparation or the oxidizing agent preparation.

In order to enable good mixing of the color changing preparation and oxidizing agent preparation, it is advantageous if the color changing preparation and oxidizing agent preparation possess good flow properties, and if the elevated viscosity of the utilization mixture is established only after the two components are mixed. One possibility for achieving this goal is the use of polymeric thickeners whose thickening properties change with pH. The color changing preparation possesses at least an acid pH in order to stabilize oxidation dye precursors, while the utilization mixture should have an alkaline pH. If the polymeric thickener is contained in the acid oxidizing agent preparation, an anionic polymeric thickener that results in a considerable increase in viscosity at an alkaline pH is therefore preferred.

Homo- or copolymers of acrylic acid or methacrylic acid are particularly suitable as such anionic polymeric thickeners. As a rule, to establish the necessary viscosity larger quantities (usually between 2 and 5 wt %) of such polymers are needed in the utilization mixture, and thus a correspondingly even greater quantity in the oxidizing agent preparation.

Large polymer loads, however, in particular of anionic polymeric thickeners, can lead to problems when manufacturing the oxidizing agent preparations, since such elevated utilization concentrations of thickeners can result, in particular with slight fluctuations in pH, in clogs in the manufacturing systems and equipment, such as dispensing pumps and valves. As well as the savings in raw materials, it is therefore particularly advantageous to use agents that have a reduced concentration of polymeric thickeners if the viscosity of the utilization mixture is not thereby impaired.

At least one object herein is therefore to furnish a two-part oxidizing coloring agent for keratinic fibers that possesses good miscibility of the two sub-components but exhibits sufficient viscosity that the agent on the one hand can be applied easily, but on the other hand remains at the location of action during utilization and does not flow out of the fibers. It is another object to provide an agent wherein the quantity of polymeric thickeners is reduced, so that the above-described problems during manufacturing of the agents can be minimized or eliminated. In addition, other objects, desirable features and characteristics will become apparent from the subsequent summary and detailed description, and the appended claims, taken in conjunction with the accompanying drawings and this background.

SUMMARY

Colorants for keratinic fibers having optimized viscosity adjustment are provided. In accordance with an exemplary embodiment, a multi-component packaging unit comprises a first container (C1) containing a color changing preparation (CCP) comprising, in a cosmetic carrier, a color-changing component and a second container (C2) packaged separately from the first container (C1) and containing an oxidizing agent preparation (OAP). The oxidizing agent preparation (OAP) comprises at least two phases separated from one another. A first phase (I) has an aqueous phase that comprises, in a cosmetically acceptable carrier, a chemical oxidizing agent and an anionic polymeric thickener chosen from homo- and copolymers of acrylic acid and methacrylic acid. A second phase (II) has a hydrophobic phase that comprises an oil chosen from paraffin oil, liquid carboxylic acid esters of $C_2$ to $C_8$ monoalkanol with a mono- or dicarboxylic acid, and combinations thereof.

In accordance with another embodiment, a method for changing a color of keratinic fibers using a multi-component packaging unit is provided. The multi-component packaging unite comprises a first container (C1) containing a color changing preparation (CCP) comprising, in a cosmetic carrier, a color-changing component. A second container (C2) packaged separately from the first container (C1) contains an oxidizing agent preparation (OAP). The oxidizing agent preparation (OAP) comprises at least two phases separated from one another. A first phase (I) has an aqueous phase that comprises, in a cosmetically acceptable carrier, a chemical oxidizing agent and an anionic polymeric thickener chosen from homo- and copolymers of acrylic acid and methacrylic acid. A second phase (II) has a hydrophobic phase that comprises an oil chosen from paraffin oil, liquid carboxylic acid esters of $C_2$ to $C_8$ monoalkanol with a mono- or dicarboxylic acid, and combinations thereof. The method comprises the steps of combining the color changing preparation (CCP) and the oxidizing agent preparation (OAP) in the first container (C1) or the second container (C2); reclosing and shaking the first container (C1) or the second container (C2) to form a ready-for-use color changing agent; applying the ready-for-use color changing agent onto the keratinic fibers; leaving the ready-for-use color changing agent onto the keratinic fibers for a contact period of about 5 to about 60 minutes; and rinsing out the ready-for-use color changing agent.

In accordance with a further embodiment, a ready-for-use agent for oxidatively changing a color of keratinic fibers is provided. The ready-for-use agent is produced immediately before use by mixing contents of containers of a multi-packaging unit comprising a first container (C1) containing a color changing preparation (CCP) comprising, in a cosmetic carrier, a color-changing component and a second container (C2) packaged separately from the first container (C1) and containing an oxidizing agent preparation (OAP). The oxidizing agent preparation (OAP) comprises at least two phases separated from one another. A first phase (I) has an aqueous phase that comprises, in a cosmetically acceptable carrier, a chemical oxidizing agent and an anionic polymeric thickener chosen from homo- and copolymers of acrylic acid and methacrylic acid. A second phase (II) has a hydrophobic phase that comprises an oil chosen from paraffin oil, liquid carboxylic acid esters of $C_2$ to $C_8$ monoalkanol with a mono- or dicarboxylic acid, and combinations thereof. The ready-for-use agent has a viscosity from about 5 to about 50 Pa·s (Brookfield, 22° C., spindle #5, 4 rpm).

In accordance with yet a further embodiment, a method for increasing a viscosity of a coloring agent for keratinic fibers is provided. The method comprises the steps of mixing a color changing preparation (CCP) comprising a color-changing component in a cosmetic carrier and an oxidizing agent preparation (OAP). The oxidizing agent preparation (OAP) has two phases separated from each other. A first phase (I) has an aqueous phase that comprises, in a cosmetically acceptable carrier, a chemical oxidizing agent and an anionic, polymeric thickener chosen from homo- or copolymers of acrylic acid, methacrylic acid, and combinations thereof. A second phase (II) has a hydrophobic phase that comprises an oil chosen from paraffin oil and liquid carboxylic acid esters of $C_2$ to $C_8$ monoalkanol with mono- or dicarboxylic acid.

DETAILED DESCRIPTION

It has now been found, in unforeseeable fashion, that by means of special two-phase cosmetic oxidizing preparations for use in color changing agents for keratinic fibers, in particular human hair, that additionally contain an oil alongside an anionic polymeric thickener, an increase in the viscosity of the ready-for-use coloring mixture is made possible. This makes it possible to reduce the quantity of anionic polymeric thickener used, without having to accept deficiencies in the viscosity of the ready-for-use coloring mixture.

In accordance with an exemplary embodiment, therefore, a multi-component packaging unit (kit of parts) contains at least two containers packaged separately from one another, where a first container (C1) comprises one color changing preparation (CCP) containing, in a cosmetic carrier, at least one color-changing component, and a second container (C2) contains an oxidizing agent preparation, wherein the oxidizing agent preparation (OAP) comprises at least two phases separated from one another, where (i) the first phase (I) represents an aqueous phase that contains, in a cosmetically acceptable carrier, at least a chemical oxidizing agent and at least an anionic polymeric thickener selected from homo- or copolymers of acrylic acid and/or methacrylic acid, and (ii) the second phase (II) represents a hydrophobic phase that contains at least one oil, selected from paraffin oil or liquid carboxylic acid esters of $C_2$ to $C_8$ monoalkanol with a mono- or dicarboxylic acid.

"Keratin-containing" or "keratinic" fibers are understood herein as furs, wool, feathers, and in particular human hair. Although the use herein is suitable principally for coloring and/or lightening keratin-containing fibers, nothing in principle conflicts with use in other sectors as well.

The color changing preparation (CCP) and oxidizing agent preparation (OAP) each contain the ingredients in a cosmetic and thus physiologically acceptable carrier. Physiologically acceptable carriers in this context are, in particular, aqueous, aqueous alcoholic, and alcoholic carriers. "Aqueous alcoholic" carriers are to be understood for purposes herein as water-containing compositions containing 3 to 70 wt % of a $C_1$ to $C_4$ alcohol, based on the total weight of the utilization mixture, in particular ethanol resp. isopropanol. An aqueous carrier contains, for purposes herein, at least 30 wt %, in particular at least 50 wt % water, based on the total weight of the utilization mixture.

In an embodiment, the color changing preparation (CCP) of the multi-component packaging unit contains at least one color-imparting component as a color-changing component. This color-imparting component is in an embodiment selected from at least one oxidation dye precursor and/or from at least one substantive dye.

An embodiment contemplated herein is therefore a multi-component packaging unit which is characterized in that the color changing preparation (CCP) contains at least one oxidization dye precursor as the color-changing component. At least one oxidation dye precursor of the developer type (developer component) is preferred as an oxidation dye precursor, preferably in combination with at least one oxidation dye precursor of the coupler type (coupler component).

Preferred oxidation dye precursors of the developer type are p-phenylenediamine derivatives. Preferred p-phenylenediamines are selected from one or more compounds of the group that is constituted from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)-amino-2-chloroaniline, 2-(2-hydroxyethyl)-p- phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxan, and physiologically acceptable salts thereof. p-Phenylenediamine derivatives contemplated herein are selected from at least one compound of the group: p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine, and physiologically acceptable salts thereof. It may furthermore be contemplated herein to use as a developer component compounds that contain at least two aromatic nuclei that are substituted with amino and/or hydroxyl groups. Exemplary binuclear developer components are selected in particular from at least one of the following compounds: N,N'-bis-(2-hydroxyethyl)-N,N'-bis-(4'-aminophenyl)-1,3-diaminopropan-2-ol, N,N'-bis(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl)tetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine, and 1,10-bis-(2',5'-diaminophenyl)-1,4,7,10-tetraoxadecane, as well as physiologically acceptable salts thereof. Further exemplary binuclear developer components are selected from among N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, or a physiologically acceptable salt thereof. It may further contemplated herein to use as a developer component a p-aminophenol derivative or a physiologically acceptable salt thereof. Exemplary p-aminophenols are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)-phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol, as well as physiologically acceptable salts thereof. Further exemplary compounds are p-aminophenol, 4-amino-3-methylphenol, 4-amino-2-aminomethylphenol, 4-amino-2-(1,2-dihydroxyethyl)phenol, and 4-amino-2-(diethylaminomethyl)phenol. The developer component can further be selected from o-aminophenol and derivatives thereof, such as e.g. 2-amino-4-methylphenol, 2-amino-5-methylphenol, or 2-amino-4-chlorophenol. The developer component can furthermore be selected from heterocyclic developer components, for example from pyrimidine derivatives, pyrazole derivatives, pyrazolopyrimidine derivatives and pyrazolopyrazole derivatives, resp. physiologically acceptable salts thereof. Exemplary pyrimidine derivatives are, in particular, the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine. Exemplary pyrazole derivatives are, in particular, the compounds that are selected from among 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, as well as physiologically acceptable salts thereof, but in particular 4,5-diamino-1-(2-hydroxyethyl)pyrazole. Exemplary pyrazolopyrimidines are the compounds selected from among pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine, as well as physiologically acceptable salts thereof and tautomeric forms thereof if a tautomeric equilibrium exists. An exemplary pyrazolopyrazole derivative is 2,3-diamino-6,7-dihydro-1H,5H-pyrazolo[1,2-a]pyrazol-1-one.

Exemplary developer components are selected from at least one compound of the group that is constituted from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, as well as physiologically acceptable salts thereof. Very particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5- diamino-1-(2-hydroxyethyl)pyrazole, as well as physiologically acceptable salts thereof.

The developer components are used, for example, in a quantity from about 0.0001 to about 2.5 wt %, for example about 0.001 to about 1.5 wt %, based in each case on the ready-for-use agent.

Coupler components alone do not produce any significant color in the context of oxidative coloring, but instead always require the presence of developer components. It is therefore contemplated herein that when at least one coupler component is used, at least one developer component is additionally utilized. Coupler components contemplated herein allow at least one chemical residue of the coupler to be substituted with the oxidized form of the developer component, in which context a covalent bond forms between the coupler component and developer component. Couplers are preferably cyclic compounds that carry on the cycle at least two groups selected from (i) optionally substituted amino groups, and/or (ii) hydroxyl groups. If the cyclic compound is a six-membered ring (preferably aromatic), the aforesaid groups are then located preferably in the ortho or meta position with respect to one another.

Coupler components contemplated herein are selected as at least one compound from one of the following classes: m-aminophenol, o-aminophenol, m-diaminobenzene, o-diaminobenzene, and/or derivatives thereof; naphthalene derivatives having at least one hydroxy group; di-resp. trihydroxybenzene; pyridine derivatives; pyrimidine derivatives; specific indole derivatives and indoline derivatives; pyrazolone derivatives (for example 1-phenyl-3-methylpyrazol-5-one); morpholine derivatives (for example 6-hydroxybenzomorpholine or 6-aminobenzomorpholine); quinoxaline derivatives (for example 6-methyl-1,2,3,4-tetrahydroquinoxaline), as well as mixtures of two or more compounds from one or more of those classes.

Exemplary m-aminophenol coupler components are selected from at least one compound from the group that is constituted from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol, and physiologically acceptable salts thereof. Preferred m-diaminobenzene coupler components are selected from at least one compound from the group that is constituted from m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, and physiologically acceptable salts thereof. Preferred o-diaminobenzene coupler components are selected from at least one compound from the group that is constituted from 3,4-diaminobenzoic acid and 2,3-diamino-1-methylbenzene and physiologically acceptable salts thereof. Preferred naphthalene derivatives having at least one hydroxy group are selected from at least one compound of the group that is constituted from 1-naphthol, 2-methyl-1-naphthol, 2-hydroxymethyl-1-naphtho 1,2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene. Preferred di-resp. trihydroxybenzenes and derivatives thereof are selected from at least one compound of the group that is constituted from resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene. Preferred pyridine derivatives are selected from at least one compound of the group that is constituted from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and physiologically acceptable salts thereof. Exemplary pyrimidine derivatives are selected from at least one compound of the group that is constituted from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, and physiologically acceptable salts thereof. Exemplary indole derivatives are selected from at least one compound of the group that is constituted from 4-hydroxyindole, 6-hydroxyindole, and 7-hydroxyindole, and physiologically acceptable salts thereof. Preferred indoline derivatives are selected from at least one compound of the group that is constituted from 4-hydroxyindoline, 6-hydroxyindoline, and 7-hydroxyindoline, and physiologically acceptable salts thereof.

Coupler components contemplated herein are selected from among 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of those compounds or physiologically acceptable salts thereof. Resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3- hydroxypyridine, and 1-naphthol, as well as a physiologically acceptable salt thereof, are very particularly preferred.

The coupler components are used, for example, in a quantity from about 0.0001 to about 2.5 wt %, such as about 0.001 to about 1.0 wt %, based in each case on the ready-for-use agent.

Developer components and coupler components are generally used in approximately molar quantities with respect to one another. Although molar utilization has proven useful, a certain excess of individual oxidation dye precursors is not disadvantageous, so that developer components and coupler components can exhibit a molar ratio from about 1 to about 0.5 to about 1 to about 3, in particular about 1 to about 1 to about 1 to about 2.

In addition, at least one substantive dye can be contained as a color-imparting component. These are dyes that absorb directly onto the hair and do not require an oxidative process for the formation of color. Substantive dyes can be subdivided into anionic, cationic, and nonionic substantive dyes. They are usually nitrophenylenediamines, nitroaminophenols, azo dyes, anthraquinones, or indophenols. The substantive dyes are used respectively in a quantity from about 0.0001 to about 2.0 wt %, preferably from about 0.001 to about 1.0 wt %, based in each case on the total application preparation.

Exemplary anionic substantive dyes are the compounds known under the international designations and/or commercial names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue. Exemplary cationic substantive dyes are cationic triphenylmethane dyes such as, for example, Basic Blue 7, Basic Blue 26, Basic Violet 2, and Basic Violet 14, aromatic systems that are substituted with a quaternary nitrogen group, for example Basic Yellow 57, Basic Red 76, Basic Blue 99, HC Blue 16 (Bluequat B), Basic Brown 16, and Basic Brown 17, as well as substantive dyes which contain a heterocycle that comprises at least one quaternary nitrogen atom, in particular Basic Yellow 87, Basic Orange 31, and Basic Red 51. The cationic substantive dyes that are marketed under the Arianor® trademark are likewise cationic substantive dyes contemplated herein. Nonionic nitro and quinone dyes, and neutral azo dyes, are particularly suitable as nonionic substantive dyes. Exemplary nonionic substantive dyes are the compounds known under the international designations and/or commercial names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol. Dye combinations contemplated herein are those that include at least the combination of tetrabromophenol blue and Acid Red 92; tetrabromophenol blue and Acid Red 98; tetrabromophenol blue and Acid Red 94; tetrabromophenol blue and Acid Red 87, or tetrabromophenol blue and Acid Red 51.

Lastly, additional bleaching power intensifiers, which intensify the action of the oxidizing agent from phase (I) of the two-phase agent, can be used as a color-changing component in lightening agents.

In an embodiment, a color changing preparation (CCP) therefore contains an additional bleaching power intensifier as a color-changing component. Additional bleaching power intensifiers that can be used in the context contemplated herein are peroxo compounds, furthermore compounds that yield aliphatic peroxocarboxylic acids under perhydrolysis conditions and/or substituted perbenzoic acid, carbonic acid derivatives, in particular carbonate salts such as hydrogen carbonate salts of ammonium, alkali, or alkaline earth metals, alkylcarbonates or -carbamates, silylcarbonates and -carbamates.

The bleaching power intensifier is, in an embodiment, selected from ammonium peroxodisulfate, alkali metal peroxodisulfates, ammonium peroxomonosulfate, alkali metal hydrogen peroxomonosulfates, alkali metal peroxodiphosphates, and alkaline earth metal peroxides. Exemplary bleaching power intensifiers are ammonium peroxodisulfate, potassium peroxodisulfate, sodium peroxodisulfate, potassium hydrogen peroxomonosulfate, potassium peroxodiphosphate, magnesium peroxide, and barium peroxide. Agents that contain as a bleaching power intensifier at least one inorganic salt selected from peroxomonosulfates and/or peroxodisulfates, are contemplated herein. In a further embodiment, the agents contemplated herein contain at least two different peroxodisulfates. Exemplary peroxodisulfate salts in this context are combinations of ammonium peroxodisulfate and potassium peroxodisulfate and/or sodium peroxodisulfate. The peroxo compounds are contained in a quantity of from about 0.1 to about 25 wt %, for example, in a quantity of from about 0.5 to about 15 wt %, based on the total weight of the ready-for-use agent.

The persulfate salts such as peroxodisulfate salts are as a rule used in anhydrous fashion and in the form of an optionally dedusted powder, a paste, or a pressed shaped element.

In a further embodiment, the color changing preparation (CCP) can contain a cationic pyridinium derivative as a bleaching power intensifier. Exemplary compounds are 4-acylpyridinium derivatives and 2-acylpyridinium derivatives. 2-acetyl-1-methylpyridinium-p-toluenesulfonate and 4-acetyl-1-methylpyridinium-p-toluenesulfonate are contemplated in this context. Further exemplary cationic pyridinium derivatives are cationic 3,4-dihydroisoquinolinium derivatives, in particular N-methyl-3,4-dihydroisoquinolinium-p-toluenesulfonate.

The bleaching power intensifiers used alongside or instead of peroxo compounds are contained in the cosmetic agents, in an embodiment, in quantities of from about 0.05 to about 10 wt %, for example, in quantities of from about 0.2 to about 5 wt %, based in each case on the total weight of the ready-for-use agent.

To further enhance the lightening performance, an optionally hydrated $SiO_2$ compound can additionally be added to the composition, in accordance with an embodiment, as a bleaching power intensifier. Although even small quantities of the optionally hydrated $SiO_2$ compounds can increase lightening performance, the optionally hydrated $SiO_2$ compounds can be used in quantities of from about 0.05 wt % to about 15 wt %, for example, in quantities of from about 0.15 wt % to about 10 wt %, such as in quantities of from about 0.2 wt % to about 5 wt %, based in each case on the anhydrous composition contemplated herein. The quantity indications reflect in each case the concentration of the $SiO_2$ compounds (without their water component) in the agents. Optionally hydrated $SiO_2$ compounds are silicic acids, oligomers and polymers thereof, and salts thereof. The optionally hydrated $SiO_2$ compounds can be present in various forms. The $SiO_2$ compounds are used according to an embodiment in the form of silica gels, or for example as water glass. Water glasses that are constituted from a silicate of the formula $(SiO_2)_n(Na_2O)_m(K_2O)_p$, where n denotes a positive rational number and m and p, mutually independently, denote a positive rational number or 0, are contemplated herein, with the provisions that at least one of the parameters m or p is different from 0, and that the ratio between n and the sum of m and p is between about 1:4 and about 4:1. Metasilicates in particular, which in accordance with the formula above are notable for a ratio between n and the sum of m and p that is less than or equal to 1, and can be construed as chain-like polymeric structures of the $[SiO_3]^{2-}$ anion, can be used with preference. Sodium metasilicate, of the formula $[NaSiO_3]_x$, is particularly preferred in this context.

A critical feature of the oxidizing agent preparation (OAP) contemplated herein of the multi-component packaging unit described above is its two-phase nature, the two phases not being miscible with one another. In an embodiment, the two phases are present in two layers one above another, with direct contact via a common interface with one another.

In the oxidizing agent preparation (OAP) according to an embodiment, phase (I) is present at least at the same weight proportion as phase (II). Phase (I) is preferably present at an excess. The weight ratio of phase (I) to phase (II) for example has a value from about 99 to about 1 to about 50 to about 50, for example from about 98 to about 2 to about 70 to about 30, such as from about 95 to about 5 to about 80 to about 20.

In accordance with an exemplary embodiment, the first phase (I) has an aqueous or aqueous alcoholic carrier. "Aqueous alcoholic" carriers are to be understood herein as water-containing compositions containing about 3 to about 70 wt % of a $C_1$ to $C_4$ alcohol, for example ethanol, such as isopropanol, based on the total weight of the utilization mixture. An "aqueous" carrier contains, for example, at least about 30 wt %, in particular at least about 50 wt % water, based on the total weight of the utilization mixture. The first phase (I) further contains a chemical oxidizing agent. The term "chemical oxidizing agent" is intended to elucidate the fact that this is a supplementary, added oxidizing agent, and not, for example, an oxidizing agent present in the environment, e.g. atmospheric oxygen. Hydrogen peroxide is an exemplary oxidizing agent as contemplated herein. Hydrogen peroxide is used either as an exemplary aqueous solution, or in the form of a solid addition compound of hydrogen peroxide with inorganic or organic compounds such as, for example, sodium perborate, sodium percarbonate, magnesium percarbonate, sodium percarbamide, polyvinylpyrrolidinone.n$H_2O$ (where n is a positive number greater than 0), urea peroxide, and melamine peroxide. Aqueous phases (I) contemplated herein contain aqueous hydrogen peroxide solutions. The concentration of a hydrogen peroxide solution is determined on the one hand by regulatory provisions and on the other hand by the desired effect. For example, about 3-wt % to about 12-wt % solutions in water are used as an aqueous phase.

An embodiment is therefore characterized in that the chemical oxidizing agent of phase (I) is selected from hydrogen peroxide and/or a solid addition product thereof with inorganic and/or organic compounds.

In an exemplary embodiment, the preparations contemplated herein contain hydrogen peroxide. Agents for changing the color of keratinic fibers that contain about 0.5 to about 18 wt %, for example about 1 to about 15 wt %, for example, about 2.5 to about 12 wt %, such as about 3 to about 9 wt % hydrogen peroxide, based on the total weight of the oxidizing agent preparation (calculated as 100% $H_2O_2$), are contemplated herein.

In a further embodiment, phase (I) of the oxidizing agent preparation (OAP) further contains an anionic polymeric thickener that is selected from homo- or copolymers of acrylic acid and/or methacrylic acid. Because the oxidizing agent preparation (OAP) usually has an acid pH but the utilization mixture has an alkaline pH, the polymeric thickener undergoes a change in pH by which the carboxylic acid groups of acrylic-acid or methacrylic-acid units are deprotonated, and gelling and thus an increase in viscosity occur as a result of that ionization.

In addition to acrylic acid and methacrylic acid, further examples of anionic monomers of which the polymeric anionic thickeners can be made are crotonic acid, itaconic acid, maleic acid anhydride, and 2-acrylamide-2-methylpropanesulfonic acid. The acid groups can be present entirely or partly as a sodium, potassium, ammonium, or mono- or triethanolammonium salt.

Exemplary anionic homopolymers are uncrosslinked and crosslinked polyacrylic acids. Allyl ethers of pentaerythritol, of sucrose, and of propylene can be exemplary crosslinking agents in this context. Such compounds are available commercially, for example, under the trademark Carbopol®.

In an exemplary embodiment, copolymers of at least one anionic monomer and at least one nonionogenic monomer may be used. With regard to the anionic monomers, reference is made to the substances listed above. Exemplary nonionogenic monomers are acrylamide, methacrylamide, acrylic acid esters, methacrylic acid esters, itaconic acid mono- and diesters, vinylpyrrolidinone, vinyl ethers, and vinyl esters.

In an embodiment, the oxidizing agent preparation contemplated herein additionally contains an anionic polymerizate or copolymerizate of acrylic acid and/or methacrylic acid. Exemplary polymerizates of this kind are:
  polymerizates of, for example, at least about 10 wt % acrylic acid low-alkyl esters, about 25 to 70 wt % methacrylic acid, and optionally up to about 40 wt % of a further comonomer,
  mixed polymerizates of about 50 to about 75 wt % ethyl acrylate, about 25 to about 35 wt % acrylic acid, and 0 to about 25 wt % of other comonomers known. Suitable dispersions of this kind are obtainable commercially, e.g. under the commercial name Latekoll® D (BASF).
  Copolymerizates of about 50 to about 60 wt % ethyl acrylate, about 30 to about 40 wt % methacrylic acid, and about 5 to about 15 wt % acrylic acid, crosslinked with ethylene glycol dimethacrylate.

Copolymers of acrylic acid, methacrylic acid, or $C_1$ to $C_6$ alkyl esters thereof, and the esters of an ethylenically unsaturated acid and an alkoxylated fatty alcohol are contemplated herein. Suitable ethylenically unsaturated acids are, in particular, acrylic acid, methacrylic acid, and itaconic acid; suitable alkoxylated fatty alcohols are, in particular, steareth-20 or ceteth-20. Copolymers of this kind are marketed by the Rohm & Haas company under the commercial name Aculyn® 22, and by the National Starch company under the commercial names Structure® 2001 and Structure® 3001.

Exemplary anionic copolymers are, for example, copolymers of acrylic acid, methacrylic acid, or $C_1$ to $C_6$ alkyl esters thereof, as marketed under the INCI declaration Acrylates Copolymers. The combination of methacrylic acid and ethyl acrylate, as well as optionally crosslinking multifunctional monomers, is suitable in this context. An exemplary commercial product for this is, for example, Aculyn® 33, such as, 33A of the Rohm & Haas company.

The anionic polymerizates or copolymerizates of acrylic acid and/or methacrylic acid are contained in the agents for example in a quantity from about 0.1 to about 10 wt %, for example from about 1 to about 6 wt %, such as from about 2.5 to about 4 wt %, based in each case on the total weight of color changing preparation (CCP) and oxidizing agent preparation (OAP).

In accordance with an embodiment, the second phase (II) of the oxidizing agent preparation (OAP) is hydrophobic in nature. The hydrophobic phase (II) is not miscible with the aqueous phase (I) containing the oxidizing agent and the anionic polymeric thickener. Hydrophobic phases—also called "lipophilic" phases—contain fatty substances that usually contain nonpolar organic compounds such as hydrocarbon compounds, long-chain triglycerides, silicone oils, esters, or ethers, as well as perhalogenated compounds.

The hydrophobic phase (II) is notable for the fact that it contains at least one liquid carboxylic acid ester of a $C_2$ to $C_8$ monoalkanol with a mono- or dicarboxylic acid, and/or at least one paraffin oil. The term "liquid" refers here to carboxylic acid esters and/or paraffin oils that are liquid at room temperature and under standard pressure. Carboxylic acid esters suitable herein are those that possess no or only very little water solubility, i.e. a water solubility of less than about 1 g per 1 L of water under standard conditions.

The liquid carboxylic acid esters contemplated herein of the hydrophobic phase (II) are derived from $C_2$ to $C_8$ monoalkanols with a mono- or dicarboxylic acid.

Examples of $C_2$ to $C_8$ monoalkanols are ethanol, n-propanol, isopropanol (1-methylethanol), 1-butanol, 2-butanol, 2-methylpropan-2-ol (tert-butanol), 2-methylpropan-1-ol (isobutanol), 1-pentanol, 2-pentanol, 3-pentanol, 3-methylbutan-1-ol (isopentanol), 3-methylbutan-2-ol (siamyl alcohol), 2-methyl-2-butanol, 2,2-dimethylpropan-1-ol (neopentyl alcohol), 1-hexanol, 4-methylpentan-1-ol (isohexanol), 1-heptanol, 1-octanol, 6-methylheptan-1-ol, 3,3-dimethylhexan-1-ol, 3,5-dimethylhexan-1-ol, 4,5-dimethylhexan-1-ol, 3-methylheptan-1-ol and 5-methylheptan-1-ol (isooctanols), and 2-ethylhexan-1-ol (ethylhexyl alcohol). Examples of suitable monocarboxylic acids are saturated fatty acids such as decanoic acid, dodecanoic acid (lauric acid), tetradecanoic acid (myristic acid), hexadecanoic acid (palmitic acid), octadecanoic acid (stearic acid), and 16-methylheptadecanoic acid (isostearic acid), unsaturated fatty acids such as palmitoleic acid (C16:1; 9Z), oleic acid (C18:1; 9Z), elaidic acid (C18:1; 9E), eicosenic acid (gondoic acid; C20:1; 11Z), linoleic acid (C18:2; 9Z, 12Z), γ(gamma)-linolenic acid (C18:3; 6Z, 9Z, 12Z), α(alpha)-linolenic acid (C18:3; 9Z, 12Z, 15Z), α-elaeostearic acid (C18:3; 9Z, 11E, 13E), and arachidonic acid (C20:4; 5Z, 8Z, 11Z, 14Z), as well as natural fatty acid cuts such as fatty acids from lanolin (lanolates), coconut fat (cocoates), and tallow (tallowates). Examples of suitable dicarboxylic acids are saturated dicarboxylic acids having 4 to 10 carbon atoms, in particular succinic acid (ethane-1,2-dicarboxylic acid), glutaric acid (propane-1,3-dicarboxylic acid), adipic acid (butane-1,4-dicarboxylic acid), and sebacic acid (octane-1,8-dicarboxylic acid).

Those carboxylic acid esters that have a total carbon number from 12 to 22 carbon atoms are suitable in this context. Contemplated compounds are ethyl laurate, propyl laurate, isopropyl laurate (IPL), butyl laurate, hexyl laurate, ethyl hexyl laurate, ethyl myristate, propyl myristate, isopropyl myristate (IPM), butyl myristate, hexyl myristate, ethyl hexyl myristate, ethyl palmitate, propyl palmitate, isopropyl palmitate (IPP), butyl palmitate, hexyl palmitate, ethyl stearate, propyl stearate, isopropyl stearate (IPS), butyl stearate, ethyl isostearate, propyl isostearate, isopropyl isostearate (IPIS), butyl isostearate, ethyl oleate, propyl oleate, isopropyl oleate (IPO), butyl oleate, diethyl succinate, dipropyl succinate, diisopropyl succinate, dibutyl succinate, dihexyl succinate, diethyl hexyl succinate, diethyl glutarate, dipropyl glutarate, diisopropyl glutarate, dibutyl glutarate, dihexyl glutarate, diethyl adipate, dipropyl adipate, diisopropyl adipate, dibutyl adipate, dihexyl adipate, diethyl sebacinate, dipropyl sebacinate, diisopropyl sebacinate, dibutyl sebacinate, and dihexyl sebacinate.

A further embodiment is characterized in that the carboxylic acid ester of the hydrophobic phase (II) is an ester of $C_3$ to $C_4$ monoalkanol with a mono- or dicarboxylic acid.

Isopropanol and butan-1-ol are suitable in particular as a $C_3$ to $C_4$ monoalkanol. Exemplary carboxylic acid esters are therefore selected from the group that is constituted from isopropyl laurate (IPL), butyl laurate, isopropyl myristate (IPM), butyl myristate, isopropyl palmitate (IPP), butyl palmitate, isopropyl stearate (IPS), butyl stearate, isopropyl isostearate (IPIS), butyl isostearate, isopropyl oleate (IPO), butyl oleate, diisopropyl succinate, dibutyl succinate, diisopropyl glutarate, dibutyl glutarate, diisopropyl adipate, dibutyl adipate, diisopropyl sebacinate, and dibutyl sebacinate. Isopropyl myristate (IPM), isopropyl palmitate (IPP), and dibutyl adipate are particularly preferred. These compounds are commercially obtainable and are marketed, among others, under the commercial names Crodamol IPM, Stepan IPM, or Lexol IPM NF resp. Rilanit IPP or Nikkol IPP, as well as Cetiol B (dibutyl adipate).

Oxidizing agent preparations contemplated herein therefore contain, as a hydrophobic phase (II), a carboxylic acid ester that is selected from the group that is constituted from isopropyl palmitate, isopropyl myristate, and dibutyl adipate.

Paraffin oils are not water-soluble, and are therefore likewise suitable as a hydrophobic phase (II) in the two-phase oxidizing agent preparations contemplated herein. The "paraffin oils" of the hydrophobic phase are to be understood as mixtures of saturated, aliphatic hydrocarbons that are liquid at room temperature. Oxidizing agent preparations contemplated herein therefore contain a paraffin oil as a hydrophobic phase (II).

A further embodiment contemplated herein is therefore a multi-component packaging unit which is characterized in that the oil of the hydrophobic phase (II) is selected from the group that is constituted from paraffin oil, isopropyl palmitate, isopropyl myristate, and dibutyl adipate.

In order to improve the separation of the hydrophilic phase (I) and hydrophobic phase (II) and reduce the tendency to form a stable emulsion, it is suitable herein if the oxidizing agent preparation contains only a small proportion of surface-active substances. "Surface-active substances" for purposes herein are considered to be emulsifiers and surfactants. Surface-active substances are notable for hydrophobic and hydrophilic structural features, and thus enable intermixing of the phases accompanied by the formation of micelles and stable emulsions. Because the embodiments herein explicitly do not encompass any oxidizing agent preparations in emulsion form, but instead contain two phases that are present separately from one another, it has proven to be particularly advantageous that the oxidizing agent preparation (OAP) contains nonionic, anionic, zwitterionic, and/or amphoteric surfactants and/or emulsifiers at a total weight of less than about 5 wt %, for example, less than about 1 wt %, based in each case on the total weight of the oxidizing agent preparation (OAP). Agents that are free of surface-active substances are particularly advantageous.

"Anionic surfactants" as used herein are all anionic surface-active substances suitable for use on the human body. These are characterized by an anionic group imparting water solubility, for example a carboxylate, sulfate, sulfonate, or phosphate group, and a lipophilic alkyl group having approximately 8 to 30 carbon atoms. Glycol ether or polyglycol ether groups, ester, ether, and amide groups, and hydroxyl groups can additionally be contained in the molecule. Examples of such anionic surfactants are, in each case in the form of the sodium, potassium, and ammonium and mono-, di, and trialkanolammonium salts having 2 to 4 carbon atoms in the alkanol group: linear and branched fatty acids having 8 to 30 carbon atoms (soaps); ethercarboxylic acids, in particular of the formula $RO(CH_2CH_2O)_xCH_2COOH$, in which R is a linear alkyl group having 8 to 30 carbon atoms and x=0 or is 1 to 16; acyl sarcosides; acyl taurides; acyl isethionates; sulfosuccinic acid mono- and dialkyl esters, and sulfosuccinic acid monoalkylpolyoxyethyl esters; linear alkanesulfonates; linear α-olefinsulfonates; sulfonates of unsaturated fatty acids; α-sulfo fatty acid methyl esters of fatty acids; alkyl sulfates and alkyl ether sulfates, in particular of the formula $RO(CH_2CH_2O)_xSO_3H$, in which R denotes a linear alkyl group having 8 to 30 carbon atoms and x denotes zero or a number from 1 to 12; mixtures of surface-active hydroxysulfonates; sulfated hydroxyalkylpolyethylene and/or hydroxyalkylenepropylene glycol ethers; esters of tartaric acid and citric acid with alcohols; alkyl and/or alkenyl ether phosphates of the formula $RO(C_2H_4O)_xP(=O)(OH)(OR')$ in which R denotes an aliphatic, optionally unsaturated hydrocarbon residue having 8 to 30 carbon atoms, R' denotes hydrogen, a $(CH_2CH_2O)_yR$ residue, and x and y mutually independently denote a number from 1 to 10; sulfated fatty acid alkylene glycol esters of the formula $RC(O)O(alkO)_nSO_3H$, in which R denotes a linear or branched, aliphatic, saturated and/or unsaturated alkyl residue having 6 to 22 carbon atoms, alk denotes $CH_2CH_2$, $CHCH_3CH_2$, and/or $CH_2CHCH_3$, and n denotes a number from 0.5 to 5; as well as monoglyceride sulfates and monoglyceride ether sulfates.

"Zwitterionic surfactants" refers to those surface-active compounds that carry in the molecule at least one quaternary ammonium group and at least one carboxylate, sulfonate, or sulfate group. Examples of such zwitterionic surfactants are the so-called betaines, such as the N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, and 2-alkyl-3-carboxymethyl-3-hydroxyethylimidazolines, having in each case 8 to 18 carbon atoms in the alkyl or acyl group, as well as cocacylaminoethylhydroxyethylcarboxymethyl glycinate. An exemplary zwitterionic surfactant is the fatty acid amide derivative known by the INCI name Cocamidopropyl Betaine.

"Amphoteric surfactants" are understood to be those surface-active compounds that contain in the molecule, in addition to a $C_8$ to $C_{24}$ alkyl or acyl group, at least one free amino group and at least one —COOH or —$SO_3H$ group, and are capable of forming internal salts. Usual amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. Examples of amphoteric surfactants are N-cocalkylaminopropionate, cocacylaminoethylaminopropionate, and $C_{12}$ to $C_{18}$ acyl sarcosine.

Nonionic surfactants and emulsifiers contain as a hydrophilic group, for example, a polyol group, a polyalkylene glycol ether group, or a combination of a polyol and polyglycol ether group. Such compounds are, for example: addition products of 1 to 50 mol ethylene oxide and/or 0 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group; addition products, end-capped with a methyl or $C_2$ to C6 alkyl residue, of 1 to 50 mol ethylene oxide and/or 0 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as, for example, the grades obtainable under the marketing designations Dehydol LS, Dehydol LT (Cognis); polyglycerol esters and alkoxylated polyglycerol esters, for example polyglyceryl-3-diisostearate (commercial product: Lameform TGI (Henkel)) and polyglyceryl-2-polyhydroxystearate (commercial product: Dehymuls PGPH (Henkel)); polyol fatty acid esters, for example the commercial product Hydagen HSP (Cognis) or Sovermol grades (Cognis); more highly alkoxylated, propoxylated, and in particular ethoxylated mono-, di-, and triglycerides having a degree of alkoxylation greater than 5, for example glycerol monolaurate+20 ethylene oxide, and glycerol monostearate+20 ethylene oxide; amine oxides; hydroxy mixed ethers; sorbitan fatty acid esters and addition products of ethylene oxide with sorbitan fatty acid esters, for example the polysorbates and sorbitan monolaurate+20 mol ethylene oxide (EO); sugar fatty acid esters and addition products of ethylene oxide with sugar fatty acid esters; addition products of ethylene oxide with fatty acid alkanolamides and fatty amines; fatty acid N-alkylglucamides; alkylphenols and alkylphenol alkoxylates having 6 to 21, in particular 6 to 15 carbon atoms in the alkyl chain and 5 to 30 ethylene oxide and/or propylene oxide units; alkylpolyglycosides corresponding to the general formula $RO—(Z)_x$, where R denotes alkyl, Z sugar, and x the number of sugar units.

Further included among the nonionic emulsifiers herein are the polymerization products of ethylene oxide and propylene oxide with saturated or unsaturated alcohols; fatty acid esters of polyvalent alcohols with saturated or unsaturated fatty acids; alkyl esters of saturated or unsaturated fatty acids or alkylphenols, and alkoxylates thereof; in particular, ethylene glycol ethers of fatty alcohols; mixed ethylene and propylene glycol ethers with fatty alcohols; fatty acid esters of sorbitan and polyethylene glycol; esters of non-hydroxylated $C_6$ to $C_{30}$ alkylmonocarboxylic acids with polyethylene glycol; and addition products of alkyl phenols with ethylene oxide and/or propylene oxide.

It may further be advantageous, in order to separate the hydrophilic and hydrophobic phase in the oxidizing agent preparation (OAP) contemplated herein, if electrolytes are additionally added. "Electrolytes" are usually understood as charged, ionic inorganic and organic compounds that contain only a very slightly expressed hydrophobic component or none at all. Preferred electrolytes are readily water-soluble salts, in particular alkali metal and alkaline earth metal salts of mineral acids and organic acids. Examples thereof are sodium chloride, sodium sulfate, sodium hydrogen sulfate, sodium carbonate, sodium hydrogen carbonate, sodium citrate, magnesium chloride, magnesium sulfate, magnesium carbonate, and magnesium hydrogen carbonate.

The oxidizing agent preparation (OAP) is notable for the fact that oil-soluble ingredients accumulate predominantly in the hydrophobic phase (II) and therefore do not come into direct contact with the oxidizing agent-containing phase (I). This is particularly advantageous for stabilizing care-providing agents in the agent that have little stability in terms of oxidation. Such preferred care-providing substances are therefore oil-soluble care-providing substances, oil-soluble vitamins, and triglycerides, in particular vegetable ones and those that contain one or more unsaturated carbon-carbon bonds. In order to make the two-phase character visually apparent, it may likewise be useful if the hydrophobic phase (II) contains oil-soluble dyes.

An exemplary embodiment is therefore characterized in that the oxidizing agent preparation (OAP) additionally contains a predominantly oil-soluble component selected from oil-soluble dyes, oil-soluble care-providing substances, oil-soluble vitamins, and triglycerides.

"Predominantly oil-soluble" refers, as used herein, to those compounds that have a water solubility of less than about 1 g per 1 L of water under standard conditions, but are readily soluble in nonpolar compounds (e.g. >about 10 g/kg of solution medium).

Oil-soluble care-providing substances are, for example, cosmetically effective terpenes and terpenoids such as, for example, bisabolol, and ubiquinones such as, for example, coenzyme Q-10.

Oil-soluble vitamins are in particular the compounds that are known by the collective terms vitamin A, vitamin D, vitamin E, and vitamin K. An agent suitable herein therefore contains at least one oil-soluble vitamin selected from vitamin A, vitamin D, vitamin E, and/or vitamin K, as well as vitamin P. "Vitamin A" encompasses retinoids, in particular all-trans-retinol. "Vitamin D," also referred to as calciferols, encompasses 7,8-didehydrosterol derivatives, in particular the compounds referred to as cholecalciferol (vitamin $D_3$, calciol), ergocalciferol (vitamin $D_2$, ercalciol), 7,8-didehydrocholesterol (provitamin $D_3$, procalciol, procholecalciferol), and ergosterol (provitamin $D_2$). Further usable vitamin D analogs are calcidiol (25-hydroxycholecalciferol), calcitriol, hydroxycalcidiol, and vitamin $D_1$ (ergocalciferol and lumisterol). "Vitamin E" is the collective term for tocopherols, and encompasses in particular the chemical compounds α-tocopherol, β-tocopherol, γ-tocopherol, δ-tocopherol, and α-tocotrienol, β-tocotrienol, γ-tocotrienol, and δ-tocotrienol. "Vitamin K" is a collective term for various compounds having vitamin K activity, which derive from 2-methyl-1,4-naphthoquinone (vitamin $K_3$). Preferred representatives are vitamin $K_{1(20)}$ (2-methyl-3-phytyl-1,4-naphthoquinone), phylloquinone (abbreviated: K),], vitamin $K_{2(35)}$ (3-all-trans-farnesylgeranylgeranyl-2-methyl-1,4-naphthoquinone), vitamin $K^3$ (2-methyl-1,4-naphthoquinone, menadione, menaphthone), and the derived analogs vitamin $K_4$ (2-methyl-1,4-naphthalenediol), vitamin $K_5$ (4-amino-2-methyl-1-naphthol), vitamin $K_6$ (2-methyl-1,4-naphthalenediamine), and vitamin $K_7$ (4-amino-3-methyl-1-naphthol). "Vitamin P" is a collective term for rutins, in particular bioflavonoids such as troxerutin (vitamin $P_4$) and hesperidin.

"Triglycerides" is the collective term for esters of glycerol, which represent the principal constituents of natural oils. Triglycerides suitable herein are those that contain at least one ester of an unsaturated fatty acid. Exemplary unsaturated fatty acids are oleic acid, linoleic acid, and linolenic acid. Vegetable oils can also be used suitably as triglycerides, in particular those that have a positive influence on the hair surface. Particularly suitable triglycerides are, in particular, oils that are obtained from the seeds of *Moringa pterygosperma* (moringa oil) or from the pits of *Argania spinosa* (argan oil). These oils are marketed, for example, under the name Lipofructyl® ARGAN LS 9779 resp. Lipofructyl® MO LS 9305 by the Cognis company.

An embodiment is therefore characterized in that the hydrophobic phase (II) additionally contains at least one oil that is selected from oils from the seeds of *Moringa pterygosperma* (moringa oil) or from the pits of *Argania spinosa* (argan oil).

The predominantly oil-soluble components are used for example at a total weight of from about 0.001 to about 10 wt %, for example of from about 0.01 to about 5 wt %, based in each case on the total weight of the hydrophobic phase (II).

According to an embodiment, the oxidizing agent preparation contains a catalyst that activates oxidation of the dye precursors, e.g. by atmospheric oxygen. Such catalysts are, for example, specific enzymes, iodides, quinones, or metal ions. Enzymes suitable for this are, for example, peroxidases, which can considerably intensify the action of small quantities of hydrogen peroxide. A use of specific metal ions or metal complexes can also be used. Metal ions are, for example, $Zn^{2+}$, $Cu^{2+}$, $Fe^{2+}$, $Mn^{2+}$, $Mn^{4+}$, $Li^+$, $Mg^{2+}$, $Ca^{2+}$, $Ce^{4+}$, $V^{3+}$, $Co^{2+}$, $Ru^{3+}$, and $Al^{3+}$. $Zn^{2+}$, $Cu^{2+}$, and $Mn^{2+}$ are particularly suitable in this context.

It has furthermore proven to be advantageous if the oxidizing agent preparations contain a stabilizer or complexing agent. Exemplary stabilizers are phenacetin, alkali benzoates (sodium benzoate), and salicylic acid.

The use of so-called complexing agents is also contemplated herein. Complexing agents are substances that can complex metal ions. Exemplary complexing agents are so-called chelate complexing agents, i.e. substances that form cyclic compounds with metal ions, where an individual ligand occupies more than one coordination site on a central atom, i.e. is at least "double-toothed." Usual chelate complexing agents that are completed herein are, for example, polyoxycarboxylic acids, polyamines, ethylenediaminetetraacetic acid (EDTA), nitrilotriacetic acid (NTA), and hydroxyethanediphosphonic acids including alkali salts thereof. Also usable are complexing polymers, i.e., polymers that carry either in the main chain itself, or laterally thereto, functional groups that can act as ligands and react with suitable metal atoms, usually accompanied by the formation of chelate complexes. The polymer-bound ligands of the resulting metal complexes can derive only from one macromolecule or can belong to different polymer chains. Complexing agents suitable for use herein are nitrogen-containing polycarboxylic acids, in particular EDTA, and phosphonates, for example, hydroxyalkane-including aminoalkanephosphonates, and in particular 1-hydroxyethane-1,1-diphosphonate (HEDP) including the di- or tetrasodium salt thereof, and/or ethylenediaminetetramethylenephosphonate (EDTMP) including the hexasodium salt thereof, and/or diethylenetriaminepentamethylenephosphonate (DTPMP) including the hepta- or octasodium salt thereof.

The preparations of the multi-component packaging unit are contained in containers packaged separately from one another. A "container" is understood in the context herein as a casing that exists in the form of an optionally reclosable bottle, a tube, a can, a pouch, a sachet, or similar casings. No limits are imposed on the casing material. The casings are, however, preferably made of glass or plastic. An embodiment in which the casing of the container that contains the color changing preparation (CCP) is transparent to the user is particularly preferred for visualization of the two-phase oxidizing agent preparation (OAP). An embodiment of the multi-component packaging unit is therefore characterized in that the first container (C2), containing the oxidizing agent preparation (OAP), has a transparent package, preferably a transparent plastic package.

It may further be suitable if the multi-component packaging unit contains at least one further hair treatment agent in a separate container, in particular a conditioning agent. The packaging unit can moreover encompass application aids, such as combs, hairbrushes, or brushes, personal protective apparel, in particular disposable gloves, and optionally a user manual.

In the context of utilization of the multi-component packaging unit, it may be immaterial whether firstly the two phases of the oxidizing agent preparation (OAP) are briefly intermixed by vigorous shaking and the color changing preparation (CCP) is added, before the phases separate again, in order to furnish the ready-for-use color changing preparation; or if firstly the two preparations are combined and the ready-for-use mixture is then produced by thorough mixing.

For improved intermixing, it is advantageous if the container (C2) that contains the two-phase oxidizing agent preparation (OAP) possesses a reclosable opening, for example a snap closure or screw closure. This enables easier addition of the color changing agent from the container (C1), which in turn exists for example in the form of a pouch or sachet in the case of anhydrous, in particular powdered color changing agents, or in the form of a tube in the case of flowable color changing agents. It is preferred to mix the individual preparations and to apply the ready-for-use agent contemporaneously onto the keratinic fibers.

In another exemplary embodiment, a method for changing the color of keratinic fibers, in particular human hair, is provided. The method is characterized in that from a multi-component packaging unit as described above, the color changing preparation and the oxidizing preparation are combined in one of the two containers (C1) and (C2), preferably in container (C2), the reclosed container is thereupon shaken, and the resulting ready-for-use color changing agent in that container is then applied onto the fibers, left on the fibers for a contact period of about 5 to about 60 minutes, and then rinsed out.

In the case of a color-imparting agent, the suitable contact time is from about 5 to about 40 minutes, for example about 10 to about 30 minutes. In the case of lightening or bleaching color changing agents, the contact time is about 30 to about 60 minutes, preferably about 40 to about 60 minutes.

Utilization temperatures can be in a range between about 15 and about 40° C. After the contact time, the color changing agent is removed from the hair by being rinsed out. Subsequent washing with a shampoo is superfluous if a highly surfactant-rich carrier was used.

A further embodiment is a ready-for-use agent for oxidatively changing the color of keratinic fibers, in particular human hair. The ready-for-use agent is produced immediately before use by mixing the components of a multi-packaging unit as described above, characterized in that it has a viscosity from about 5 to about 50 Pa·s, for example about 10 to about 20 Pa·s (Brookfield, 22° C., spindle #5, 4 rpm).

The agents have a viscosity that permits easy application and distribution of the agent onto the fibers to be colored, but at the same time ensures retention at the desired site of action during the utilization period. The agents thus have good utilization viscosity values, and are notable for a reduced concentration of anionic polymeric thickener.

The agents therefore for example have a viscosity from about 5 to about 50 Pa·s, preferably about 10 to about 20 Pa·s. To make the measurement results more easily comparable, the viscosities recited herein were each measured with the DV–II+Pro viscosimeter of the Brookfield company, using spindle #5 at 4 rpm (revolutions per minute) at room temperature (22° C.) in 590 ml beakers (tall).

Ready-for-use agents as contemplated herein are aqueous, flowable preparations. The agents can further contain all active substances, additives, and adjuvants known for such preparations. The ready-for-use agents, constituting a mixture of color changing preparation and the oxidizing agent preparation, can contain surface-active substances selected from the anionic, nonionic, zwitterionic, and amphoteric surfactants listed above.

Cationic surfactants of the quaternary ammonium compound, esterquat, and amidoamine types are suitable in ready-for-use agents. Exemplary quaternary ammonium compounds are ammonium halides, in particular chlorides and bromides, such as alkyltrimethylammonium chlorides, dialkyldimethylammonium chlorides, and trialkylmethylammonium chlorides, as well as the imidazolium compounds known by the INCI names Quaternium-27 and Quaternium-83. The quaternized protein hydrolysates represent further cationic surfactants usable herein. Alkylamidoamines are usually manufactured by amidation of natural or synthetic fatty acids and fatty acid cuts with dialkylaminoamines, such as stearamidopropyldimethylamine. Esterquats, also preferred, are quaternized ester salts of fatty acids with triethanolamine, quaternized ester salts of fatty acids with diethanol alkylamines, and quaternized ester salts of fatty acids with 1,2-dihydroxypropyldialkylamines Such products are marketed, for example, under the trademarks Stepantex, Dehyquart and Armocare. The products Armocare VGH-70—an N,N-bis(2-palmitoyloxyethyl)dimethylammonium chloride—and Dehyquart F-75, Dehyquart C-4046, Dehyquart L80, and Dehyquart AU-35, are examples of such esterquats. The cationic surfactants are contained in the agents contemplated herein for example in quantities of from about 0.05 to about 10 wt %, based on the entire agent. Quantities of from about 0.1 to about 5 wt % are particularly suitable.

In an embodiment, nonionic, zwitterionic, and/or amphoteric surfactants, as well as mixtures thereof, can be preferred.

Further active substances, adjuvants, and additives that are usable are, for example, nonionic polymers (such as vinylpyrrolidinone/vinyl acrylate copolymers, polyvinylpyrrolidinone and vinylpyrrolidinone/vinyl acetate copolymers, and polysiloxanes); zwitterionic and amphoteric polymers (such as acrylamidopropyltrimethylammonium chloride/acrylate copolymers and octylacrylamide/methyl methacrylate/tert-butylaminoethyl methacrylate/2-hydroxypropyl methacrylate copolymers); anionic polymers (such as polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methylvinyl ether/maleic acid anhydride copolymers, and acrylic acid/ethyl acrylate/N-tert-butylacrylamide terpolymers); thickeners (such as agar-agar, guar gum, alginates, xanthan gum, gum arabic, karaya gum, locust bean flour, linseed gums, dextrans, cellulose derivatives, e.g. methyl cellulose, hydroxyalkyl cellulose, and carboxymethyl cellulose, starch fractions and derivatives such as amylose, amylopectin, and dextrins, clays such as e.g. bentonite, or entirely synthetic hydrocolloids such as, for example, polyvinyl alcohol); structuring agents (such as sugars, maleic acid, and lactic acid) and consistency agents (such as sugar esters, polyol esters, or polyol alkyl ethers); protein hydrolysates (in particular hydrolysates of elastin, collagen, keratin, milk protein, soy protein, and wheat protein, condensation products thereof with fatty acids); perfume oils; cyclodextrins; solvents and solubilizers (such as ethanol, isopropanol, ethylene glycol, propylene glycol, glycerol, dimethyl isosorbide, and diethylene glycol); defoamers such as silicones; dyes and pigments for coloring the agent; anti-dandruff active substances (such as piroctone olamine, zinc omadine, und climbazol); light-protection agents (in particular derivatized benzophenones, cinnamic acid derivatives, and triazines); active substances (such as allantoin, pyrrolidonecarboxylic acids, cholesterol, and salts thereof); further fats and waxes (such as fatty alcohols, beeswax, Montan wax, and paraffins); swelling and penetration substances (such as glycerol, propylene glycol monoethyl ether, carbonates, hydrogen carbonates, guanidines, ureas, and primary, secondary, and tertiary phosphates); opacifiers (such as latex, styrene/PVP and styrene/acrylamide copolymers); luster agents (such as ethylene glycol mono- and distearate as well as PEG-3 distearate); propellants (such as propane/butane mixtures, $N_2O$, dimethyl ether, $CO_2$, and air), and antioxidants.

One skilled in the art will arrive at a selection of these further substances in accordance with the desired properties of the agents. With regard to further optional components, as well as the quantities of those components used, reference is made expressly to the relevant manuals known to one skilled in the art, e.g. Kh. Schrader, Grundlagen und Rezepturen der Kosmetika [Cosmetics fundamentals and formulations], 2nd ed., Hüthig Buch Verlag, Heidelberg, 1989.

The ready-for-use agents made up of the color changing preparation and the oxidizing agent preparation preferably have a pH in the range of from about 6 to about 12. Agents suitable herein are characterized in that they have an alkaline pH. A further embodiment of the present agent consists in the fact that the ready-for-use agent has a pH between about 7.0 and about 12.0, for example between about 8.0 and about 11.0. The pH values for purposes herein are pH values that were measured at a temperature of 22° C.

The pH is usually adjusted using pH adjusting agents. One skilled in the art is familiar, for purposes of adjusting the pH, with acidifying and alkalizing agents common in cosmetics. The alkalizing agents usable for adjusting the pH are typically selected from inorganic salts, in particular of the alkali and alkaline-earth metals, organic alkalizing agents, in particular amines, basic amino acids and alkanolamines, and ammonia. Acidifying agents suitable herein are edible acids such as, for example, citric acid, acetic acid, malic acid, or tartaric acid, as well as dilute mineral acids.

Organic alkalizing agents usable herein are preferably selected from alkanolamines of primary, secondary, or tertiary amines with a $C_2$ to $C_6$ alkyl base element that carries at least one hydroxyl group. Exemplary alkanolamines are selected from the group: 2-amino ethan-1-ol (monoethanolamine), 2-amino-2-methylpropan-1-ol, and 2-amino-2-methylpropane-1,3-diol). A particularly suitable alkanolamine is monoethanolamine Suitable basic amino acids are lysine, arginine, and ornithine. The inorganic alkalizing agents are selected form the group that is constituted from sodium hydroxide, potassium hydroxide, calcium hydroxide, barium hydroxide, sodium phosphate, potassium phosphate, sodium silicate, potassium silicate, sodium carbonate, and potassium carbonate.

The addition of oil to an anionic polymeric thickener allows a reduction in the quantity of polymeric anionic thickener used. The result is on the one hand that raw material quantities can be decreased, and on the other hand that problems caused in manufacturing methods by large quantities of anionic thickener can be minimized.

A further embodiment is therefore the use of an oxidizing agent preparation (OAP) having two phases separated from one another, where (i) the first phase (I) represents an aqueous phase that contains, in a cosmetically acceptable carrier, a chemical oxidizing agent and an anionic, polymeric thickener selected from homo- or copolymers of acrylic acid and/or methacrylic acid, and (ii) the second phase (II) represents a hydrophobic phase that contains an oil, selected from paraffin oil or liquid carboxylic acid esters of $C_2$ to $C_8$ monoalkanol with a mono- or dicarboxylic acid to increase the mixed viscosity of a coloring agent for keratinic fibers, which agent is produced by mixing a color changing preparation (CCP) containing, in a cosmetic carrier, a color-changing component, and said oxidizing agent preparation (OAP).

EXAMPLES

1) Color Cream FC (Quantities Indicated in wt %)

| | |
|---|---|
| Lanette D | 6.60 |
| Lorol C12-18 techn. | 2.40 |
| Eumulgin B 2 | 0.60 |
| Eumulgin B 1 | 0.60 |
| Akypo Soft 45HP | 10.00 |
| Protelan MST 35 | 6.00 |
| Texapon K 14 S Special, 70% | 2.80 |
| Product W 37194 | 3.75 |
| Sodium sulfite, anhydrous | 0.00 |
| Ascorbic acid | 0.10 |
| HEDP, aqueous, 60% | 0.20 |
| Sodium silicate 40/42 | 0.50 |
| Potassium hydroxide, aqueous, 50% | 1.00 |
| Glycine | 1.00 |
| Taurine | 1.00 |
| alpha-Lipoic acid | 0.20 |
| Litchiderm LS 9704 | 1.00 |
| p-Toluylenediamine sulfate | 2.81 |
| 2,4-Diaminophenoxyethanol 2HCl | 0.44 |
| Resorcinol | 1.00 |
| m-Aminophenol | 0.20 |
| Monoethanolamine | 9.20 |
| Perfume | q.s. |
| Water, deionized | to 100 |

Raw materials:
Lanette D (INCI name: Cetearyl Alcohol; Cognis);
Lorol C12-18 techn. (INCI name: Coconut Alcohol; Cognis);
Eumulgin B 2 (INCI name: Ceteareth-20; Cognis);
Eumulgin B 1 (INCI name: Ceteareth-12; Cognis);
Akypo Soft 45HP (approx. 21%, INCI name: Sodium Laureth-6 Carboxylate, Aqua; KAO);
Protelan MST 35 (approx. 35%, INCI name: Sodium Myristoyl Sarcosinate, Sodium Methyl Cocoyl Taurate, Aqua; Zschimmer & Schwarz);
Texapon K 14 S Special (approx. 70%, INCI name: Sodium Myreth Sulfate, Aqua; Cognis);
Product W 37194 (approx. 20%, INCI name: Acrylamidopropyltrimonium Chloride/Acrylates Copolymer, Aqua; Stockhausen);
Litchiderm LS 9704 (INCI name: Butylene Glycol; Litchi Chinensis Pericarp Extract; Laboratoires Serobiologiques).

The fat base was melted together at 80° C. and dispersed with a portion of the quantity of water. The remaining formula constituents were then incorporated in sequence while stirring. Water was added to bring up to 100 wt %, and the formulation was stirred until cold.

2) Developer Preparations EW (Quantities Indicated in wt %)

| Raw material | V1 | E1 | E2 | E3 |
|---|---|---|---|---|
| Caustic soda 45% techn. | 0.73 | 0.73 | 0.73 | 0.73 |
| Dipicolinic acid | 0.10 | 0.1 | 0.10 | 0.10 |
| Disodium pyrophosphate | 0.03 | 0.03 | 0.03 | 0.03 |
| HEDP, aqueous, 60% | 1.50 | 1.5 | 1.50 | 1.50 |
| Texapon NSO | 2.00 | 2.00 | 2.00 | 2.00 |
| Dow Corning DB 110 A | 0.07 | 0.07 | 0.07 | 0.07 |

-continued

| Raw material | V1 | E1 | E2 | E3 |
|---|---|---|---|---|
| Aculyn 33A | 15.00 | 15.00 | 15.00 | 13.00 |
| Hydrogen peroxide, aqueous, 50% | 12.00 | 12.00 | 12.00 | 12.00 |
| Liquid paraffin | — | 16.66 | — | — |
| Isopropyl myristate | — | — | 16.66 | 16.66 |
| Water, deionized | to 100 | to 100 | to 100 | to 100 |

Raw materials:
Texapon NSO (approx. 27%, INCI name: Sodium Laureth Sulfate; Cognis);
Aculyn 33A (approx. 28%; INCI name: Acrylates Copolymer, Aqua; Rohm & Haas);
Dow Corning DB 110 A (INCI name: Dimethicone; Dow Corning).

3) Utilization Mixtures:

Before use, the developer solutions E1, E2, E3, and V1 were added respectively to the color cream FC at room temperature at a 1:1 weight ratio, and thoroughly mixed.

The following mix viscosities were obtained:

| Coloring agent | Utilization mixture | Mix viscosity* (mPa · s) | Change as compared with mix viscosity of comparison agent |
|---|---|---|---|
| #1 | FC + V1 (not inventive) | 17100 | — |
| #2 | FC + E1 (inventive) | 20100 | +17.5% |
| #3 | FC + E2 (inventive) | 19900 | +16.4% |
| #4 | FC + E3 (inventive) | 17200 | +0.6% |

*measured with a Brookfield DV-II + Pro viscosimeter with spindle #5 at 4 rpm at room temperature (22° C.) in 590 ml beakers (tall).

The ready-for-use coloring agents #2 resp. #3 thus exhibit a distinctly elevated viscosity as compared with the comparison coloring agent #1. The coloring agent #4 demonstrates that as a result of adding IPM, even with a 13% reduction in the quantity of anionic polymeric thickener used, an equivalent viscosity can still be achieved in the utilization mixture.

The invention claimed is:

1. A multi-component packaging unit comprising:
a first container (C1) containing a color changing preparation (CCP) comprising, in a cosmetic carrier, a color-changing component;
a second container (C2) packaged separately from the first container (C1) and containing an oxidizing agent preparation (OAP), wherein the oxidizing agent preparation (OAP) comprises at least two phases separated from one another, wherein:
a first phase (I) has an aqueous phase that comprises, in a cosmetically acceptable carrier, a chemical oxidizing agent and an anionic polymeric thickener chosen from homo- and copolymers of acrylic acid and methacrylic acid; and
a second phase (II) has a hydrophobic phase that comprises an oil chosen from paraffin oil, liquid carboxylic acid esters of $C_2$ to $C_8$ monoalkanol with a mono- or dicarboxylic acid, and combinations thereof.

2. The multi-component packaging unit according to claim 1, wherein the color-changing component comprises an oxidization dye precursor.

3. The multi-component packaging unit according to claim 1, wherein the chemical oxidizing agent of the first phase (I) is chosen from hydrogen peroxide, a solid addition product thereof with inorganic and/or organic compounds, and combinations thereof.

4. The multi-component packaging unit according to claim 1, wherein the anionic polymeric thickener of the first phase (I) is chosen from copolymers of at least two different monomers, chosen from acrylic acid, methacrylic acid, $C_1$ to $C_4$ alkyl esters of acrylic acid, $C_1$ to $C_4$ alkyl esters of methacrylic acid, and combinations thereof.

5. The multi-component packaging unit according to claim 1, wherein the oil of the hydrophobic phase is chosen from paraffin oil, isopropyl palmitate, isopropyl myristate, and dibutyl adipate.

6. The multi-component packaging unit according to claim 1, wherein the oxidizing agent preparation (OAP) comprises nonionic, anionic, zwitterionic, and/or amphoteric surfactants and/or emulsifiers at a total weight of less than about 5 wt % based on the total weight of the oxidizing agent preparation (OAP).

7. The multi-component packaging unit according to claim 6, wherein the oxidizing agent preparation (OAP) comprises the nonionic, anionic, zwitterionic, and/or amphoteric surfactants and/or emulsifiers at the total weight of less than about 1 wt % based on the total weight of the oxidizing agent preparation (OAP).

8. The multi-component packaging unit according to claim 1, wherein the first container (C1) has a transparent package.

9. The multi-component packaging unit according to claim 8, wherein the first container (C1) has a transparent plastic package.

10. A method for changing a color of keratinic fibers using a multi-component packaging unit comprising:
a first container (C1) containing a color changing preparation (CCP) comprising, in a cosmetic carrier, a color-changing component;
a second container (C2) packaged separately from the first container (C1) and containing an oxidizing agent preparation (OAP), wherein the oxidizing agent preparation (OAP) comprises at least two phases separated from one another, wherein:
a first phase (I) having an aqueous phase that comprises, in a cosmetically acceptable carrier, a chemical oxidizing agent and an anionic polymeric thickener chosen from homo- and copolymers of acrylic acid and methacrylic acid; and a second phase (II) having a hydrophobic phase that comprises an oil chosen from paraffin oil, liquid carboxylic acid esters of $C_2$ to $C_8$ monoalkanol with a mono- or dicarboxylic acid, and combinations thereof,
the method comprising the steps of:
combining the color changing preparation (CCP) and the oxidizing agent preparation (OAP) in the first container (C1) or the second container (C2);
reclosing and shaking the first container (C1) or the second container (C2) to form a ready-for-use color changing agent;
applying the ready-for-use color changing agent onto the keratinic fibers;
leaving the ready-for-use color changing agent onto the keratinic fibers for a contact period of about 5 to about 60 minutes; and
rinsing out the ready-for-use color changing agent.

11. The method according to claim 10, wherein applying comprises applying the ready-for-use color changing agent onto human hair.

12. A ready-for-use agent for oxidatively changing a color of keratinic fibers, wherein the ready-for-use agent is produced immediately before use by mixing contents of containers of a multi-packaging unit comprising a first container (C1)

containing a color changing preparation (CCP) comprising, in a cosmetic carrier, a color-changing component; and
   a second container (C2) packaged separately from the first container (C1) and containing an oxidizing agent preparation (OAP), wherein the oxidizing agent preparation (OAP) comprises at least two phases separated from one another, wherein:
   a first phase (I) has an aqueous phase that comprises, in a cosmetically acceptable carrier, a chemical oxidizing agent and an anionic polymeric thickener chosen from homo- and copolymers of acrylic acid and methacrylic acid; and
   a second phase (II) has a hydrophobic phase that comprises an oil chosen from paraffin oil, liquid carboxylic acid esters of $C_2$ to $C_8$ monoalkanol with a mono- or dicarboxylic acid, and combinations thereof, and
wherein the ready-for-use agent has a viscosity from about 5 to about 50 Pa·s (Brookfield, 22° C., spindle #5, 4 rpm).

13. The ready-for-use agent according to claim 12, wherein the ready-for-use agent is for oxidatively changing a color of human hair.

14. The ready-for-use agent according to claim 12, wherein the ready-for-use agent has the viscosity of from about 10 to about 20 Pa·s.

15. A method for increasing a viscosity of a coloring agent for keratinic fibers, the method comprising the steps of:
   mixing a color changing preparation (CCP) comprising a color-changing component in a cosmetic carrier and an oxidizing agent preparation (OAP), the oxidizing agent preparation (OAP) having two phases separated from each other, wherein a first phase (I) has an aqueous phase that comprises, in a cosmetically acceptable carrier, a chemical oxidizing agent and an anionic, polymeric thickener chosen from homo- or copolymers of acrylic acid, methacrylic acid, and combinations thereof, and wherein a second phase (II) has a hydrophobic phase that comprises an oil chosen from paraffin oil and liquid carboxylic acid esters of $C_2$ to $C_8$ monoalkanol with mono- or dicarboxylic acid.

* * * * *